United States Patent

Larson et al.

[11] Patent Number: 6,039,694
[45] Date of Patent: Mar. 21, 2000

[54] COUPLING SHEATH FOR ULTRASOUND TRANSDUCERS

[75] Inventors: Margaret J. Larson, Lummi Island; John W. Rutter, Bellingham; Larry L. Smith, Seattle, all of Wash.

[73] Assignee: Sonotech, Inc., Bellingham, Wash.

[21] Appl. No.: 09/104,686

[22] Filed: Jun. 25, 1998

[51] Int. Cl.$^7$ .................................................. A61B 8/14
[52] U.S. Cl. ........................................... 600/459; 73/644
[58] Field of Search ................................. 600/459, 462, 600/466; 73/644; 607/152; 604/20; 601/2

[56] References Cited

U.S. PATENT DOCUMENTS

| | | |
|---|---|---|
| 4,002,221 | 1/1977 | Buchalter . |
| 4,370,451 | 1/1983 | Stoy . |
| 4,459,854 | 7/1984 | Richardson et al. . |
| 4,593,699 | 6/1986 | Poncy et al. . |
| 5,039,774 | 8/1991 | Shikinami et al. ............... 600/459 |
| 5,078,149 | 1/1992 | Katsumata et al. ............... 600/459 |
| 5,207,225 | 5/1993 | Oaks et al. . |
| 5,252,692 | 10/1993 | Lovy et al. . |
| 5,259,383 | 11/1993 | Holstein et al. . |
| 5,482,047 | 1/1996 | Nordgren et al. . |
| 5,522,878 | 6/1996 | Montecalvo et al. . |
| 5,676,159 | 10/1997 | Navis . |

OTHER PUBLICATIONS

Echo Ultrasound Catalog, vol. 10, p. 16.
Cone Instruments Catalog, vol. 17, 1996, p. 26.

*Primary Examiner*—Marvin M. Lateef
*Assistant Examiner*—Ali M. Imam
*Attorney, Agent, or Firm*—Robert L. McDowell

[57] ABSTRACT

A homogeneous, solid, elastic, biocompatible sheath which is conformal and performs as if integral to the diagnostic and/or therapeutic medical ultrasound transducer, and comprised of 20 to 95% biocompatible liquid, preferably about 70% to about 95% biocompatible liquid, that render properties to the sheath resulting in the desirable level of acoustic coupling, with acceptable low levels of acoustic artifacts, distortion and attenuation and provides a microbial barrier between the transducer and a surgical field or skin. Such sheaths are fabricated from a group of hydrophilic block co-polymers whose chemistry and physical properties provide ability to form products by dipping, casting, molding or extrusion. The device of this invention is a conformal ultrasound acoustic energy coupling and microbial barrier sheath that replaces gel or fluid ultrasound couplants and/or protective latex or synthetic elastomer covers, which require placement of ultrasound coupling fluids or gels between the cover and the transducer as well as between the cover and the body. The invention eliminates biological reactions from latex contact and harmful gel or fluid couplant spills into body orifices, organs, tissue and blood. The inventive sheath is sterilizable, replaceable, disposable, biocompatible, and leaves no harmful residue when used within the body orifices, intraoperatively, or during biopsy and aspiration, and remains lubricous when in contact with water based fluids.

35 Claims, 2 Drawing Sheets

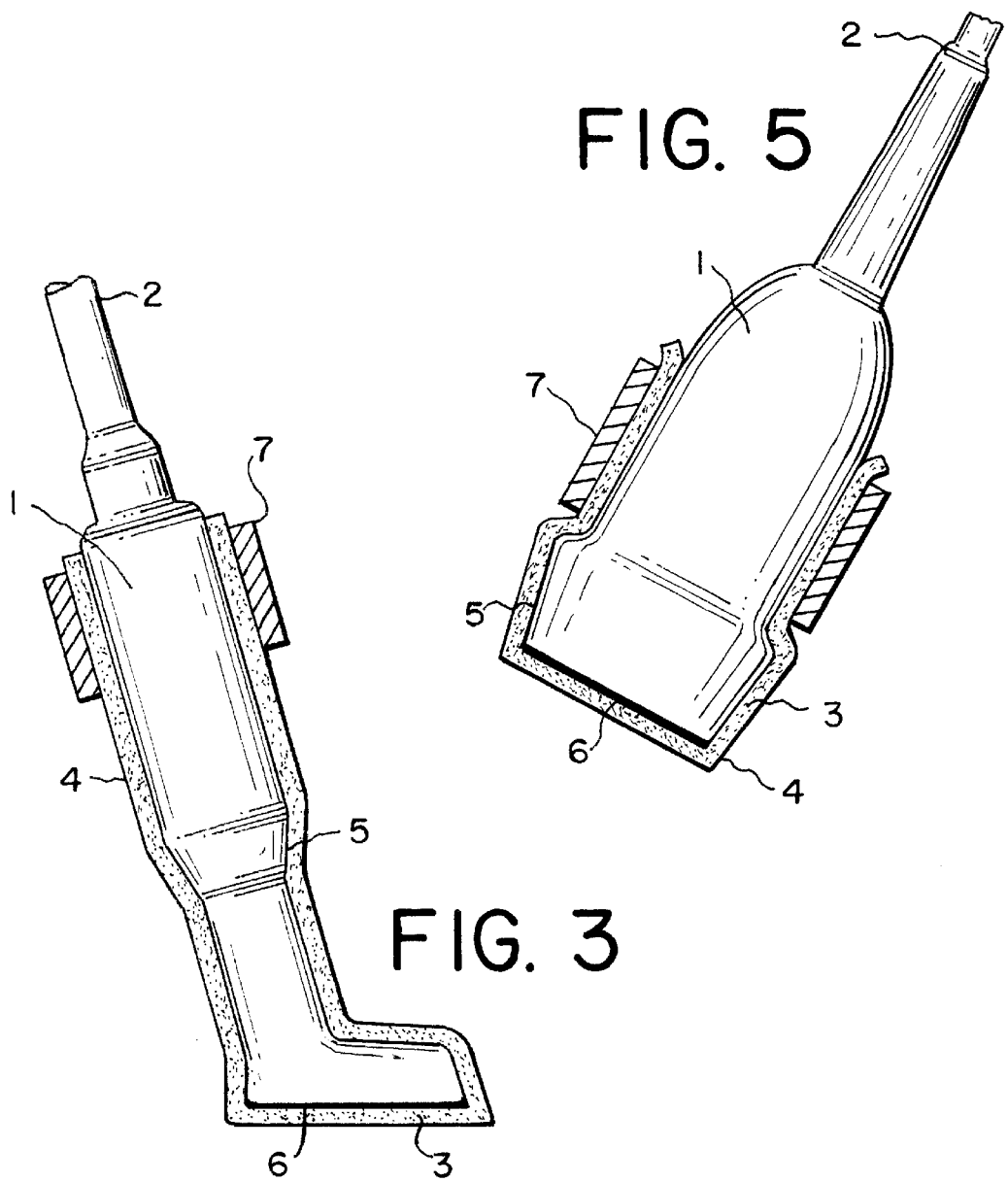
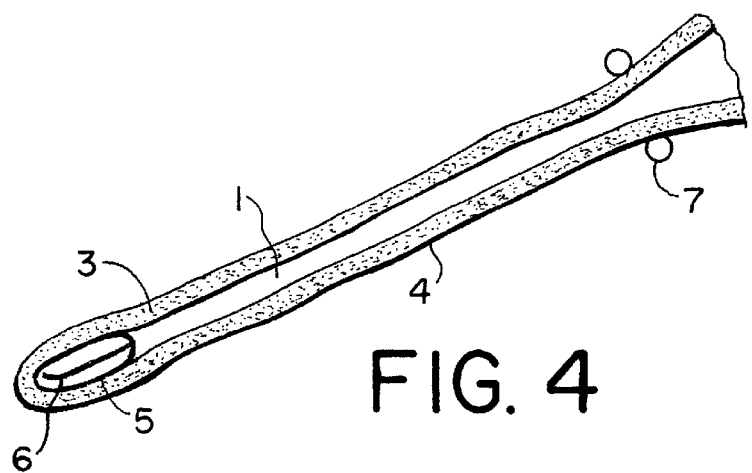

COUPLING SHEATH FOR ULTRASOUND TRANSDUCERS

FIELD OF THE INVENTION

The present invention is directed to the medical use of ultrasound acoustic energy for imaging, doppler based flow measurement, and therapy. In particular, the present invention pertains to an acoustic conducting or coupling microbial barrier sheath for ultrasound transducers.

BACKGROUND OF THE INVENTION

Ultrasound, as used for medical applications, utilizes high frequencies, typically between 1 and 30 MHz for imaging and flow measurements, and between 0.05 and 1.00 MHz for therapy, all of which are poorly transmitted by air and require a conduction medium similar in acoustic properties to tissue, commonly a thick fluid or gel. The ultrasound coupling gel or fluid displaces air and fills contours between the piezoelectric eye or transducer of an ultrasound instrument (such as a probe or scanhead), which converts energy between electrical and acoustic, and the body into which the sound is being directed. Examples of ultrasound probes or scanheads can be found in U.S. Pat. No. 5,482,047 to Nordgren et al. or U.S. Pat. No. 5,207,225 to Oaks et al. This gel or fluid material, by nature of its physical and acoustic properties, serves as an ultrasound acoustic coupler between the ultrasound transducer and tissue, thereby acoustically joining the two, so that the ultrasound based information developed can freely pass back and forth between the body and the transducer.

Because of the coupling effect, this media is commonly referred to as an ultrasound couplant, ultrasound gel, scanning gel, ultrasound transmission media or acoustic transmission media. Many fluids and water-based gels have been used as ultrasound couplants over the years. Early use of mineral oil was replaced by gels whose thickness was provided from a polymer group consisting of a copolymer of methyl vinyl ether, maleic anhydride, carboxy polymethylene polymer and mixtures thereof, or from a mixture of carboxy polymethylene polymer neutralized with an alkaline agent as a primary thickener together with hydroxy alkyl cellulose as an auxiliary thickener and a polyalkylene glycol such as propylene glycol as a humectant, as described in U.S. Pat. No. 4,002,221 to Buchalter and U.S. Pat. No. 4,459,854 to Richardson et al.

Biopsy, aspiration, amniocentesis and other puncture procedures guided with ultrasound, and ultrasound imaging procedures conducted during surgery currently use a combination of latex or synthetic elastomeric covers and forms of commercial fluids or gels external to the cover for coupling the ultrasound from the transducer to the patient. Hence, as a puncturing needle passes through the gel on the skin of the patient, minute quantities of the gel may be carried into the underlying tissue and the body cavity thereby introducing a likely tissue-incompatible substance into the patient.

Furthermore, since latex and synthetic elastomer covers in current use do not couple ultrasound adequately and uniformly over the entire active area of a transducer, a commercial coupling fluid or gel must also be inserted between the active surface of the transducer and the cover. Such covers containing commercial coupling fluids or gels occasionally rupture, tear, or are cut while being used for intraoperative, intracavity, or biopsy procedures, rendering the patient at risk from exposure to fluid or gel couplant chemicals introduced into the body, which are not typically biocompatible. In addition to an acoustic coupling fluid or gel between the transducer and the latex or synthetic elastomer cover, an additional acoustic coupling fluid, gel, or a lubricating jelly between the exterior of the cover and tissue is often required. The application of chemical ultrasound coupling fluids, gels and lubricating jelly, and the presence of latex, talc and associated compounds create documented problems of biological incompatibility which can be immediately life threatening as well as have severe long term consequences to the patient.

Fluids and gels commonly used as ultrasound couplants have several fundamental disadvantages, some of which are described below.

1. Fluids and gels offer no microbial barrier between the patient and the transducer; thus, latex rubber or synthetic elastomer probe covers must be applied over the transducer, to prevent transmission of microorganisms to the patient. In the prior art, two layers of couplant, one inside and one outside the cover, are required to provide ultrasound acoustic coupling between transducer and the patient. This potential infection concern is readily apparent when the transducer is used for imaging during needle biopsy or aspiration, or inside the body during surgery in direct organ, tissue and blood contact. Of growing importance is the protection from infection by skin transmission to patients who are immune compromised by disease, organ replacement, immune system modification, chemotherapy or radiation treatments.

2. Fluids or gels are difficult to contain on, and remove from the patient during and after the ultrasound procedure, and introduce problems to the electronics by their chemically degrading nature.

3. Commercially available oils and water based gels may react with the adhesives, elastomers, and epoxies used in the construction of medical ultrasound transducers, thus appreciably degrading performance and shortening their service life.

4. Fluids or thickened water-based gels typically used in medical ultrasound, similarly described as in U.S. Pat. No. 4,002,221, are comprised of chemical compounds such as acrylic polymers, carboxy alkyl cellulose, hydroxyethylcellulose, carboxy polymethylene, organic acids, alkali metal salts, parabens and other germicidal and fungicidal agents, and surfactants. Such chemicals are not approved, or suitable for use in applications where they may be carried into the body, such as during biopsy, intra-operative procedures, or when the transducer is placed inside a body orifice. In instances where sterile latex rubber or synthetic covers containing thickened ultrasound coupling gels are used in surgery, tearing, cutting, or rupture of the cover results in the tissue incompatible ultrasound coupling gel spilling into the body cavity. During ultrasound guided needle biopsy, aspiration, intracavity and intra-operative procedures, sterile covers produced from latex, polyurethane, polypropylene and other polymers, such as described in U. S. Pat. No. 4,593,699 to Poncy et al., U.S. Pat. No. 5,259,383 to Holstein et al. and U.S. Pat. No. 5,676,159 to Navis, are used with such tissue incompatible gel chemicals. A puncturing needle can carry such chemicals into the body, such as into the breast or into amniotic fluid, since gels are present on the skin of the patient at the point of needle insertion, as well as between the transducer and the sheath to accomplish ultrasound acoustic coupling.

5. Solid couplant hydrogels in sheet form that are placed directly upon and remain on the skin of the patient, during the ultrasound exam, such as those described in U.S. Pat. No. 5,522,878 to Montecalvo et al., solid film-coupling gel layer combinations such as disclosed in Echo Ultrasound catalog, Volume 10, page 16 or Cone Instruments catalog, Volume 17, 1996, page 26, and fluids and ultrasound gels placed directly on the patient can create non-uniform layers with wrinkles and/or entrapped air between the transducer and patient which may result in degradation of the acoustic information.

It is an object of the present invention to combine the ultrasound couplant, the protective microbial barrier and lubrication into one homogenous, uniform, integral, solid sheath which is a passive, sterilizable and disposable media that conducts or couples the ultrasound acoustic energy between a transducer and a body.

It is another object of the present invention to provide an ultrasound couplant sheath that is applied to the transducer as a microbial barrier so that the integral solid ultrasound coupling nature of the conformal sheath eliminates the need for a protective cover and separate ultrasound couplant, and blocks the transmission of pathogens or from patient to patient in the routine external non-invasive use of medical ultrasound.

It is a further object of the present invention to provide a solid, conformal sheath that is attached to the transducer and which moves over the exam surface as a part of the transducer, thus providing uniform and reproducible coupling over the entire active surface of the transducer that is in contact with the site being examined.

SUMMARY OF THE INVENTION

The present invention is a homogeneous, elastic solid sheath which is conformal, sterilizable and disposable, and performs as if integral to the diagnostic and/or therapeutic medical ultrasound transducer. The inventive sheath comprises 20 to 95% biocompatible liquid and is fabricated from a group of hydrophilic acrylic acid derived block co-polymers whose chemistry and physical properties provide the ability to form products by dipping, casting, molding or extrusion. The mechanical and chemical properties of these sheaths can be optimized relative to specific products and processes by adjustment in polymer percentage, water and alkali salt content and chemical modifiers.

The inventive device is an integration of ultrasound couplant, lubricant and sterilizable microbial barrier into one elastic, form-fitting, solid sheath device that is acoustic coupling (i.e. transmits and receives ultrasound acoustic energy between the medical ultrasound transducer and the body) while remaining lubricous when in contact with body fluids, and provides a physical microbial barrier between the target (e.g. patient) and the medical transducer.

The invention provides a homogenous, uniform, elastic, solid, lubricous, ultrasound coupling sheath that is integral to and conformal to a diagnostic and/or therapeutic medical ultrasound transducer. The coupling sheath is comprised of a hydrophilic acrylic acid derived block co-polymer, preferably polyacrylonitriles, and 20 to 95% water or saline resulting in a desirable level of acoustic coupling, with an acceptable low level of acoustic distortion and attenuation, as the ultrasound energy passes between the transducer and the tissue. Preferred forms of this invention can consist of transducer conformable sheaths of controlled thickness, or preformed sheath shapes of hydrogel, having a controlled thickness that demonstrate the capacity to withstand the mechanical rigors of medical ultrasound procedures while possessing acoustic properties similar to that of human tissue and rendering desirable low levels of artifact, distortion and attenuation of the ultrasound energy.

BRIEF DESCRIPTION OF THE DRAWINGS

FIG. 3 illustrates a pre-formed, solid, conformal hydrogel sheath that encloses, surrounds and tightly conforms to a complex geometry transducer.

FIG. 4 illustrates the pre-formed hydrogel sheath of this invention in the form of a solid conforming hydrogel sheath that surrounds and tightly conforms to the shape of an intracavity transducer body.

FIG. 5 illustrates the homogenous, conformal solid hydrogel sheath of this invention pre-formed to a generic shape and size that covers the active surface of a range of transducers.

DETAILED DESCRIPTION OF INVENTION

The present invention will now be discussed in detail with reference to the accompanying drawings wherein like components will be referenced by the same reference numbers. Unless otherwise specified, percents given are based on weight.

A homogenous, elastic, lubricous, solid ultrasound coupling sheath is provided that is conformal and performs as if integral to the medical imaging, flow detection, or therapeutic medical ultrasound transducer. The ultrasound coupling sheath is a hydrophilic polymer comprised of 20 to 95% (preferably 70 to 95%) biocompatible liquid, preferably water or saline and most preferably saline, which renders properties to the sheath that produce a desirable level of ultrasound acoustic coupling with an acceptable low level of acoustic artifacts, distortion, and attenuation. The sheaths of this invention provide an ultrasound coupling microbial barrier that replaces protective latex or synthetic covers and fluid or gel-type ultrasound couplants used between the cover and the transducer and between the cover and the body. The integral, solid, acoustic coupling sheath of the invention provides a coupling media that is sterilizable and biocompatible with tissue and body fluids (e.g. blood). When used within body orifices, intraoperatively and during biopsy or aspiration procedures, the invention of an integral solid coupling sheath introduces no harmful residue and remains lubricous throughout its use and is removed and disposed of after a one-time use. The sheaths of the present invention also replace fluid and gel couplants in standard, non-sterile medical ultrasound procedures.

The acoustic properties (e.g. impedance) of the inventive sheath are generally equivalent to the acoustic properties of the target. That is, the acoustic properties of the sheath are within an acceptable range of the acoustic properties of the target (e.g. human tissue) so as not to cause distortion or artifacts to the ultrasound.

Figure 1:
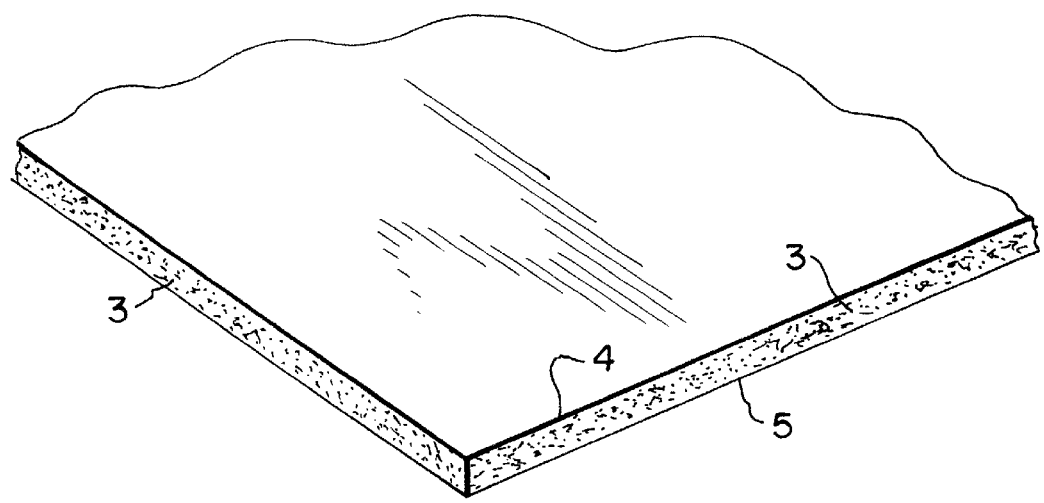
FIG. 1 illustrates a sheet form of the conformable, flexible, elastic, lubricating, solid, acoustic coupling hydrogel sheath embodied in this invention.

FIG. 1 illustrates a sheet form of the conformable, flexible, elastic, lubricating, uniform, acoustic coupling hydrogel sheet 3 embodied in this invention. The hydrogel sheath preferred in the embodiment of this invention is a polymer having a multi block structure. Such a polymer is a chain consisting of a combination of two types of sequences, one sequence being the organized crystalline regions (the "hard blocks") which are responsible for mechanical properties, the other sequence (known as the "soft blocks") forming amorphous regions that are responsible for flexibility, swelling and other properties. Persons skilled in the art will recognize the variety of potential combinations available for polymers having such block structure. The family of polymers preferred on the embodiment of this invention are those in which the hard blocks have a polyacrylonitrile structure that is highly structural providing high cohesive energy. The soft blocks are composed of hydrophilic groups derived from acrylic acids such as acrylamide and its derivatives, acrylates and acrylic esters. Each polymer chain is composed of several sequences of units with pendant nitrile groups (hard blocks) and several sequences of pendant hydrophilic groups (soft blocks).

The hydrogel sheaths of this invention are produced with a preferred controlled thickness of 0.05 to 4.0 mm throughout. The hydrogel sheet 3 is homogenous in composition throughout and on all surfaces 4, 5 thus providing equal and uniform acoustic energy coupling capacity throughout. The hydrogel sheath 3 of this invention provides a desirable level of acoustic coupling with low acceptable levels of artifact and distortion, when applied and integrally conformed to ultrasound transducers of different sizes and shapes, while also providing a solid microbial barrier sheath between the transducer and the patient, and a lubricous interface between the transducer and the patient.

Figure 2:
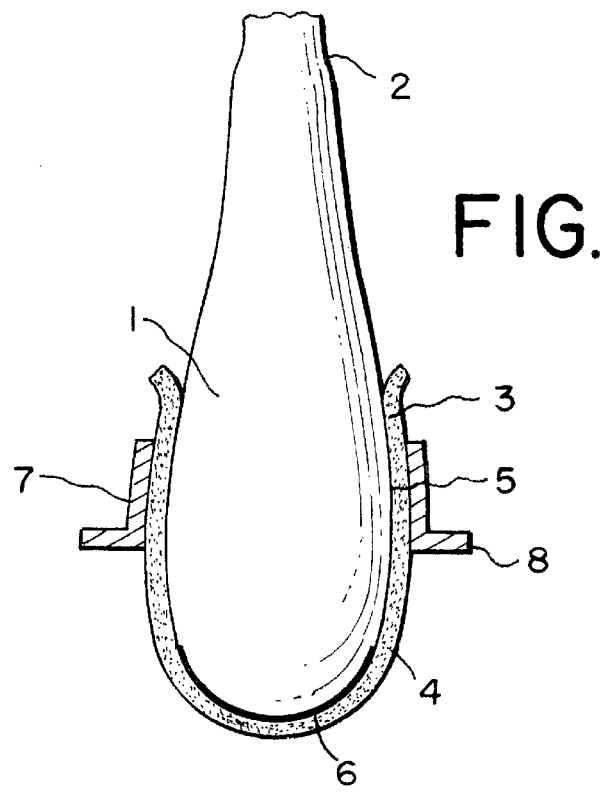
FIG. 2 illustrates a second form of the embodiment whereas the active surface of the transducer and the transducer are covered with a homogenous, elastic, solid coupling sheath of the invention.

FIG. 2 illustrates a transducer 1 with connecting cable 2 wherein the active surface 6 of the transducer and a portion of the transducer body 1 are covered with a homogenous, uniform, elastic, coupling sheath 3 of the invention that is first prepared as a flat sheet of hydrogel (FIG. 1) having a controlled thickness, typically 0.05 to 4.0 mm, preferably 0.50 mm, and then stretched to conform to the active transmitting and receiving surface 6 of the transducer 1 and attached to the transducer body 1 with a retainer 7. The retainer 7 can be in the form of a clip with finger rests 8, an elastomeric band, or any other means capable of holding the solid acoustic hydrogel sheath 3 against the active surface of the transducer 6 in such a manner that acoustic coupling is continually maintained between the entire active surface of the transducer 6 and the conformable, acoustic coupling microbial barrier hydrogel sheath 3 of this invention.

The conformal hydrogel sheets 3 can be applied in sizes and thickness as necessary to cover the active surface 6 and body 1 of the transducer, and securely attached to the transducer body such as with a retainer 7. The solid conformable ultrasound coupling hydrogel sheath 3, used in this form of the embodiment, is uniform in composition within and on all surfaces 4, 5, and in use, is applied to the medical ultrasound transducer active surface 6 and body 1, conforming the sheath 3 over the active area 6 of the transducer by stretching, manipulating and securing the hydrogel sheath 3 to the body 1 of the transducer with a retainer 7.

FIG. 3 illustrates a pre-formed, solid, conformal hydrogel sheath 3 that encloses, surrounds and closely conforms to a complex geometry transducer that is used during surgery, as described by previously mentioned U.S. Pat. No. 5,482,047, and in such a manner that the sheath becomes integral to the body 1 of the transducer, and the active surface 6, and forms a solid ultrasound coupling sheath that is lubricous, provides a microbial barrier, and couples a desirable level of acoustic energy between the transducer and the target. The present invention is readily formable to these complex designs. The inventive hydrogel conformal sheath covers all or a portion of the transducer body 1 and is held in such manner by a retainer 7, so as to maintain uniform, constant and integral contact of the solid hydrogel ultrasound coupling sheath 3 with the transducer's active surface 6 during the ultrasound procedure. The conformal hydrogel sheath 3 covers the transducer's active surface 6, and the sheath's outer surface 4 provides lubricity and a pathway for acoustic energy conduction or coupling and a solid microbial barrier between the transducer and the target.

FIG. 4 illustrates the pre-formed hydrogel sheath of this invention in the form of a solid conforming hydrogel sheath 3 that surrounds and closely conforms to the shape of an intracavity transducer body 1, as described in previously mentioned U.S. Pat. No. 5,207,225, attached by a retainer 7 and is conformal to the active surface 6 of the transducer producing a continuous, coupling acoustic hydrogel sheath layer 3 and physical microbial barrier between the transducers active area 6, the body 1 of the transducer and the patient. The external surface 4 covering the entire medical ultrasound transducer body 1 is lubricous, reducing or eliminating the need for lubricants.

FIG. 5 illustrates the uniform, homogeneous, conformal solid hydrogel sheath 3 of this invention pre-formed to a generic shape and size that covers the active surface 6 of a range of transducers, providing for acoustic coupling between the active area 6 of the transducer and the conformable hydrogel acoustic layer 3 and also providing a solid microbial barrier between the patient and the transducer. A retainer 7 may be attached to maintain conformity of the acoustic coupling ultrasound hydrogel sheath 3 to the active area 6 of the transducer. With the acoustic coupling and lubricous properties of the present invention, the need for separate gel or fluid couplants is reduced or eliminated.

Sheaths of the present invention have physical and mechanical properties that impart characteristics required by physical rigors of medical ultrasound procedures and the requirements of an ultrasound couplant. Sheaths of this invention preferably possess a water or saline content of about 70% to about 95% and acoustic properties that provide the desired levels of acoustic energy coupling between the transducer and the tissue without causing unacceptable acoustic artifacts, attenuation or data distortion. Sheaths having these characteristics transfer or couple acoustic energy readily between the transducer and tissues when uniformly conformed to the active area of the transducer. Such conformance may be achieved by forming the acoustic sheath to the shape of the transducer to achieve an integral fit, or by stretching the flat conformable sheath over the active elements of the transducer then securing said sheath to the transducer body with a retaining device. The integral conformance of the invention of a uniform homogeneous lubricating hydrogel sheath to the face of the transducer produces an interface that efficiently couples ultrasound between the electronics and the patient. Sheaths of this invention range preferably between 0.05 and 4.0 mm in thickness and may be made uniform in thickness and acoustic properties throughout the area where the acoustic energy is coupled, by selection of polymer concentration, polymer composition, percentage of water or saline, and miscible compounds, and techniques of casting and molding the sheath.

During diagnostic or therapeutic use, the invention of a conformal, homogenous, integral solid ultrasound coupling sheath will be subjected to mechanical stresses induced by stretching, bending and abrasion. These stresses dictate that the conformed, solid ultrasound coupling sheaths used in this invention, have properties of tensile strength, yield strength and elongation sufficient to provide the strength and flexibility required to accomplish the procedure with unlikely failure of the sheath by fracture or tearing. Polymer sheaths of this use will typically have tensile strengths in the range of 15 to 65 Kg/sq. cm, tear strength of greater than 100 Kg/cm and elongation at break in excess of 1100%. Hydrogel sheaths preferred in the embodiment of this invention are ultrasound acoustic coupling preformed and conformal sheaths that are able to maintain high tear strength and elongation values due to dissipation of applied stress by slip. If the situation should present itself where the maximum tear strength of the hydrogel is exceeded, failure of the hydrogel will occur by tearing gradually rather than fracturing in a catastrophic manner. Transducer or probe sheets such as those described in previously discussed U.S. Pat. No. 5,522,878 are produced from natural and synthetic polymers that typically covalently crosslink during formation of the hydrogel. Such crosslinked hydrogels as described in this patent tend to break in a catastrophic manner, rather than gradually tear, and at stress levels less than that required to fracture the hydrogels in the preferred embodiment of this invention.

The inventive sheaths are ultrasound coupling, provide a desirable level of acoustic coupling to and from the transducer and patient, and provide a physical and microbial barrier between the transducer and the patient. Because of the high liquid content (preferably about 70% to about 95%) the sheath surfaces are slippery, providing lubricity. The transducer is physically and biologically separated by the solid sheath barrier from direct contact with the skin, mucosa, organs, connective tissue and/or body fluids during ultrasound procedures. Additionally, due to the inherent slippery nature and acoustic coupling capacity of the polymer sheath, ultrasound procedures may be performed without ultrasound coupling gel or fluid chemicals between the transducer elements and the sheath, or between the sheath and the patient. The chemical structure and composition of the invention provides biocompatibility with human tissue and can be sterilized by E-beam (electron beam), heat (e.g. autoclaving), and gamma irradiation. Ultrasound coupling sheaths and conforming shapes as provided by this invention are thus rendered sterile by commercial processes providing use and application as sterile barrier sheaths in general ultrasound, intraoperative and intracavity imaging, and ultrasound guided biopsy and aspiration procedures.

In a preferred embodiment of the invention, the polymer is based on a family of hydrophilic acrylate derivatives that as a molecule are structured such that a backbone of nitrile groups are sequenced with a series of attached hydrophilic units that function as reaction sites. The size of the nitrile groups and variability of the hydrophilic side groups such as acrylates, acrylamide and acrylic esters, together with modifications to the manufacturing process produce polymers that demonstrate a range of physical and mechanical properties. The nitrile group structure produces cohesive strengths that approximate the energy levels of covalent, crosslinked hydrogels. These attributes produce hydrogels with exceptional tensile, elongation, and tear strength properties. The combination of excellent mechanical properties with attendant water and/or saline contents ranging from about 70% to about 95%, sheaths of these polymers exhibit the properties required to survive mechanical manipulation without catastrophic failure by tearing. Liquid contents of 70% and more in the sheaths is key to the close acoustic match. The family of polymers in the preferred embodiment of this invention are hydrophilic acrylic acid derived block co-polymers such as those described in U.S. Pat. No. 5,252,692 to Lovy et al. or U.S. Pat. No. 4,370,451 to Stoy. Of these hydrophilic acrylic acid derived block co-polymers, the most preferred is polyacrylonitrile co-polymer which is a known and commercially available polymer.

Hydrogel sheaths preferred in the embodiment of this invention can be cast as sheets with con,trolled thickness, typically 0.05 to 4.0 mm of various lengths and widths, as well as dip and rotational cast or extruded, to form shapes which conform closely to the shape of specific medical ultrasound transducers. The inventive hydrogel sheaths provide ultrasound acoustic coupling and lubricity with acceptable low levels of artifact, distortion and attenuation, and a physical microbial barrier that is equivalent for each shape, size and form.

As previously mentioned, the polymer is based on a family of hydrophilic acrylate derivatives that as a molecule are structured such that a backbone of nitrile groups are sequenced with a series of attached hydrophilic units that function as reaction sites. The size of the nitrile groups and variability of the hydrophilic side groups such as acrylates, acrylamide, acrylic esters and others contribute to the mechanical properties. Hydrogel sheaths preferred in the embodiment of this invention are produced from hydrophilic block copolymers in the form of "pre-polymer" solutions that contain water, a solvent such as (but not limited to) sodium thiocynate (NaSCN) typically in amounts of up to 55%, and usually between 2% and 35% block co-polymer, preferably about 5% to about 12% and most preferably about 8% to about 12%, comprising the above mentioned nitrile groups and hydrophilic side groups. such pre-polymer solutions are known and are commercially available.

Hydrogel flat sheets are typically formed by continuous membrane casting of a desired thickness on a support polymer or backing, or individual casts of polymer solution onto a support such as glass then drawn to desired thickness. To coagulate the hydrogel, the support and cast film is submersed into a water, or preferably saline (0.45% to 0.9% NaCl) bath at 45° C. and allowed to remain in water for a period of time of about 3 minutes or more, depending upon the film thickness, to complete its coagulation. The sheet is finished by washing in water or, preferably, saline (0.45% to 0.9% NaCl), with repeated changes of rinse water, until the rinse water contains no trace of NaSCN, which may be determined by conductivity testing.

When the sheets are produced by continuous casting methods, typically the pre-polymer solution is cast onto a non-woven backing, then onto a rotating drum that is partially submersed in water or saline. The rotational speed and diameter of the drum is of sufficient size to allow coagulation of the polymer sufficient to permit stripping of the sheet and subsequent transfer of the sheet to spools for washing and further processing.

Pre-formed, conformal sheath shapes can be formed by conventional methods of mold coagulation, rotational casting, extrusion and dipping. One hydrogel sheath forming method used in manufacture of the solid homogenous, lubricous, coupling, pre-formed, conformal sheaths of this invention is dipping. Mandrels consisting of the desired shape of the transducer, with the appropriate dimensional allowances for shrinkage, are dipped into the polymer solution, withdrawn and subsequently manipulated to allow the polymer to spread evenly over the surface of the shaped mandrel. The polymer is then coagulated, in place, by immersion in water or saline as discussed above. When the polymer has coagulated, it can remain in place or be stripped from the mandrel prior to washing with water or saline to remove NaSCN or other solvents. The final size of the formed hydrogel sheath can be larger, smaller or the same as the size of the mandrel on which it was formed depending on the saline concentration and whether the original volume of the solvent in the polymer solution was smaller, equal to or greater than the volume of the saline or water needed to swell the polymer. Once washed, the formed, conformal hydrogel sheath may be further processed for packaging as a non-sterile sheath or sterilized by E-beam (electron beam), heat (e.g. autoclaving) or gamma ray.

In use, pre-formed hydrogel sheath shapes or flat sheets are placed over the transducer in a manner that physically conforms, and produces an acoustic coupling between the ultrasound transducer and the body. The hydrogel sheath, containing hydrophilic acrylic acid derived block co-polymer solids and as much as about 95% water or saline, preferably 8% to 12% hydrophilic acrylic acid derived block co-polymer polyacrylonitrile solids and 88% to 92% saline, creates its own acoustic coupling and lubrication, thus eliminating the need to apply commercial coupling fluids or gels inside or external to the hydrogel sheath. If additional hydration or lubricity is desired, sterile saline, which is compatible with tissue and blood, can be applied.

Unlike commercial ultrasound coupling fluids or gels, the hydrogel sheaths preferred in the embodiment of this invention are biocompatible. The sheaths of this invention eliminate patient exposure to coupling fluids and gels as they conduct and couple ultrasound energy, are free of harmful residue, and provide a microbial barrier. The inventive sheaths are easily removed from the transducer after each use, thus they are a replaceable and disposable single-use sheath.

This invention provides a hydrogel sheath that is pre-formed to the shape of the medical transducer, or a hydrogel in sheet form that is conformed by stretching to the active area and body of the transducer, providing an integral, biocompatible sheath that performs as an acoustic coupling medium, microbial barrier, and lubricant between the medical transducer and the patient. The conformal sheaths formed by the hydrogel sheets of this invention are acoustically coupling, thus eliminating the need to use ultrasound couplant fluids or gels. The slippery and lubricous nature of the external surface of the conformal sheath in contact with organs, body fluid, and mucosa eliminate the need for lubricants as they remain lubricous, and acoustically coupling throughout use when in contact with water based fluids. For applications in routine, external, non-sterile use in medical ultrasound, the skin can be wetted with sterile saline or water in liquid or spray form if additional moisture is required by the hydrogel sheath.

An additional advantage of the present invention is that the solid integral ultrasound coupling sheath eliminates much, if not all, of the patient and electronic equipment contamination from present commercially available fluids and gels, subsequent clean up, and corrosive or harmful effect on the electronic equipment. Furthermore, the solid conformal, ultrasound acoustic coupling sheath of the present invention is a tissue and body fluid compatible device that eliminates use of gels and coupling fluids for such procedures and leaves no residue after the device of this invention is removed from the surgical field. During biopsy, sterile saline fluid, which is compatible with all tissues, may be used in conjunction with the invention, which eliminates carrying non-biocompatible commercially available coupling fluids and gels into the body via a biopsy or aspiration needle.

Yet another advantage is that the solid integral ultrasound coupling sheath confines the chemical environment of the transducer only to that of saline or water, thereby eliminating contact with and transmission of skin borne pathogens during routine, non-invasive use of medical ultrasound as well as eliminating contact with and chemical attack by glycols, surfactants, oils, and acrylic polymers typically used in commercial ultrasound gel and fluid couplants, thus reducing or eliminating cleaning the transducer in chemically degrading solutions to remove dried gel, chemicals, pathogens and other contaminants.

It is to be understood that while the present invention has been discussed with reference to medical or therapeutic ultrasound applications with human tissue as a target, it is not to be limited thereto. The present invention is also contemplated with other animal tissue such as in veterinary ultrasound or with industrial applications such as sheaths for industrial transducers.

While the invention has been described with reference to preferred embodiments it is to be understood that the invention is not limited to the particulars thereof. The present invention is intended to include other suitable hydrogels and polymers and modifications which would be apparent to those skilled in the art to which the subject matter pertains without deviating from the spirit and scope of the appended claims.

What is claimed is:

1. A homogeneous, elastic, ultrasound coupling sheath having a shape which is conformal to a medical ultrasound transducer, said sheath comprising a hydrophilic block co-polymer and 20 wt. % to about 95 wt. % biocompatible liquid and having acoustic properties generally equivalent to acoustic properties of a predetermined target, said sheath being lubricous when in contact with said target and providing a microbial barrier between said transducer and said target when said sheath is conformed to said transducer and placed in contact with said target, said sheath being replaceable and disposable.

2. The sheath of claim 1 comprising about 70 wt. % to about 95 wt. % biocompatible liquid.

3. The sheath of claim 2 wherein said biocompatible liquid comprises water or saline.

4. The sheath of claim 3 comprising 90 wt. % to 92 wt. % saline.

5. The sheath of claim 1 comprising said block co-polymer in an amount of 2 wt. % to 35 wt. %.

6. The sheath of claim 1 wherein said block co-polymer comprises acrylic acid block co-polymer.

7. The sheath of claim 6 comprising said acrylic acid block co-polymer in an amount of about 8 wt. % to about 12 wt. %.

8. The sheath of claim 7 wherein said acrylic acid block co-polymer comprises polyacrylonitrile.

9. The sheath of claim 1 having a thickness of 0.05 mm to 4.0 mm.

10. The sheath of claim 9 having a thickness of 0.1 mm to 2.0 mm.

11. The sheath of claim 1 wherein said sheath is sterilizable.

12. The sheath of claim 1 wherein said sheath is biocompatible with human tissue and body fluids.

13. The sheath of claim 1 having a form substantially identical to at least an active area of said transducer and wherein said sheath is positioned over and in contact with at least said active area and provides acoustic coupling between said active area and said target when said transducer is functionally positioned adjacent said target, said sheath providing said acoustic coupling in the absence of other acoustic coupling substances.

14. The sheath of claim 13 having a uniform thickness in at least that portion of the sheath in contact with said active area.

15. The sheath of claim 1 wherein said sheath is single-use.

16. The sheath of claim 1 wherein said sheath is positioned to conform to at least an active area of said transducer and wherein said sheath is positioned over and in contact with at least said active area and provides acoustic coupling between said active area and said target when said transducer is functionally positioned adjacent said target, said sheath providing said acoustic coupling in the absence of other acoustic coupling substances, said sheath being held in the conformal position by at least one retaining means.

17. The sheath of claim 16 wherein said retaining means comprises an elastomeric band or a clip.

18. The sheath of claim 17 wherein said clip includes finger rests.

19. The sheath of claim 1 wherein said transducer is a diagnostic ultrasound transducer or a therapeutic ultrasound transducer.

20. A homogeneous, elastic, replaceable and disposable ultrasound coupling sheath having a predetermined form which is generally the same as the form of at least an active portion of a predetermined medical ultrasound transducer, said sheath comprising a hydrophilic block co-polymer and about 70 wt. % to about 95 wt. % biocompatible liquid and having acoustic properties generally equivalent to acoustic properties of a predetermined target, said sheath being lubricous when in contact with said target, said sheath form being of a size whereby said sheath form is elastically stretched in order to position said sheath form about said transducer in a manner in which a portion of said sheath form is in intimate contact with said active area of said transducer, said sheath form remaining positioned about said transducer by virtue of its elastic stretched condition.

21. The sheath of claim 20 wherein said sheath provides a microbial barrier between said transducer and said target.

22. The sheath of claim 20 wherein said biocompatible liquid comprises water or saline.

23. The sheath of claim 22 comprising 90 wt. % to 92 wt. % saline.

24. The sheath of claim 20 wherein said hydrophilic block co-polymer comprises a hydrophilic acrylic acid block co-polymer in an amount of 2 wt. % to 35 wt. %.

25. The sheath of claim 24 wherein said hydrophilic acrylic acid block co-polymer comprises polyacrylonitrile in an amount of 5 wt. % to 12 wt. %.

26. A homogeneous, elastic, replaceable and disposable sheath comprising a hydrophilic block co-polymer and about 70 wt. % to about 95 wt. % biocompatible liquid and having acoustic properties generally equivalent to acoustic properties of a predetermined target, said sheath being in the form of a flat sheet of sufficient size whereby said sheath is elastically stretched in a position about a medical ultrasound transducer in a manner in which a portion of said sheath is in intimate contact with an active area of said transducer, said sheath form remaining positioned about said transducer by virtue of a retaining means, said sheath being lubricous when in contact with said tissue.

27. The sheath of claim 26 wherein said sheath provides a microbial barrier between said transducer and said target.

28. The sheath of claim 26 wherein said biocompatible liquid comprises water or saline.

29. The sheath of claim 28 comprising 90 wt. % to 92 wt. % saline.

30. The sheath of claim 26 wherein said block co-polymer comprises a hydrophilic acrylic acid block co-polymer in an amount of 2 wt. % to 35 wt. %.

31. The sheath of claim 30 wherein said hydrophilic acrylic acid block co-polymer comprises polyacrylonitrile in an amount of 5 wt. % to 12 wt. %.

32. A homogeneous, elastic, replaceable and disposable sheath having a predetermined form which is generally the same as the form of at least an active portion of a plurality of predetermined medical ultrasound transducers of varying sizes, said sheath comprising a hydrophilic block co-polymer and about 70 wt. % to about 95 wt. % biocompatible liquid and having acoustic properties generally equivalent to acoustic properties of a predetermined target, said sheath being lubricous when in contact with said target, said sheath being elastically stretchable in a position about said medical ultrasound transducers in a manner in which a portion of said sheath is in intimate contact with an active area of said transducers, said sheath form remaining positioned about said transducers by virtue of a retaining means, said sheath being lubricous when in contact with said target.

33. The sheath of claim 32 wherein said sheath provides a microbial barrier between said transducer and said target.

34. A method of conducting ultrasound energy between an ultrasound transducer and a target, said method comprising:

providing said transducer with an active area for transmitting, or transmitting and receiving, said ultrasound energy, covering at least said active area with an ultrasound coupling sheath comprising a hydrophilic block co-polymer and about 70 wt. % to about 95 wt. % biocompatible liquid and having acoustic properties generally equivalent to acoustic properties of said target, placing the covered transducer active area in contact with said target, and, transmitting, or transmitting and receiving, said ultrasound energy respectively to and/or from said target through said ultrasound coupling sheath in the absence of other ultrasound coupling substances, whereby said sheath is lubricous when in contact with said target and provides a microbial barrier between said transducer and said target.

35. The method of claim 34 wherein said block co-polymer comprises a hydrophilic acrylic acid block co-polymer in an amount of 2 wt. % to 35 wt. %.

* * * * *